United States Patent [19]

Wight et al.

[11] Patent Number: 5,223,412

[45] Date of Patent: Jun. 29, 1993

[54] CELL-FREE AND WHOLE CELL ICE NUCLEATORS AND PROCESS FOR THEIR PRODUCTION

[75] Inventors: David R. Wight, Rochester; Wayne R. Newman, Pittsford; Patrick J. Ward, Rochester; Kristine Pochodylo, Penfield, all of N.Y.

[73] Assignee: Genencor International, Inc., South San Francisco, Calif.

[21] Appl. No.: 658,652

[22] Filed: Feb. 21, 1991

[51] Int. Cl.$^5$ .................... C12R 21/04; C12R 1/18; C12R 1/38; C12N 15/00

[52] U.S. Cl. .................. 435/71.1; 435/69.1; 435/172.3; 435/252.33; 435/252.34; 435/847; 435/874; 530/324; 530/828; 252/70

[58] Field of Search ............ 435/69.1, 71.1, 847, 435/172.3, 874, 252.34, 252.33; 252/70; 530/324, 828

[56] References Cited

U.S. PATENT DOCUMENTS

| | | | |
|---|---|---|---|
| 4,021,304 | 5/1977 | Shimamatsu et al. | 195/28 |
| 4,045,910 | 9/1977 | Arny et al. | 435/847 |
| 4,062,727 | 12/1977 | Srinivasan et al. | 195/28 |
| 4,200,228 | 4/1980 | Woerpel | 239/25 |
| 4,464,473 | 8/1984 | Orser et al. | 435/172.3 |
| 4,706,463 | 11/1987 | Lindsey | 435/260 |
| 4,766,077 | 8/1988 | Orser et al. | 435/874 |
| 4,784,943 | 11/1988 | Warren et al. | 435/172.3 |
| 4,796,805 | 1/1989 | Carlberg et al. | 239/2.2 |
| 4,978,540 | 12/1990 | Lee | 435/847 |

OTHER PUBLICATIONS

Abe et al. (1989) "An ice nucleation active gene of *Erwinia ananas;* Pseudomonas species and regions required for ice nucleation activity", FEBS, 258: 297-300.

Arai et al. (1986) "Freeze Texturing of Food Materials by Ice-Nucleation with the Bacterium *Erwinia ananas*", Agri. Biol. Chem., 50: pp. 159-175.

Broeze et al. (1978) "Effects of Low Temperature on In Vivo and In Vitro Protein Synthesis of *Escherichia coli* and Pseudomonas fluorescens," Journal of Bacteriology, 134.

Burdett et al (1974) "Electron Microscope Study of Septum Formation in *Escherichia coli* Strains B and B/r During Synchronous Growth", Outer Structures of Bacteria, pp. 191-195.

Forsberg et al (1981) "Cellulase and Xylanase Release from *Bacteroides succinogenes* and its Importance in the Rumen Environ.", Applied & Environmental Microbiology: pp. 886-896.

Herendeen et al. (1979) "Levels of Major Proteins of *Escherichia coli* During Growth at Different Temperatures", Journal of Bacteriology, 139: pp. 185-194.

Jung (1990) "Preliminary Field Experiments of Snomax TM on Cumulus Mediocris Clouds to Artificially Induce the Production of Ice particles", J. Weather Mod., 22: pp. 153-157.

Kozloff et al. (1983) "Ice Nucleating Activity of *Pseudomonas syringae* and *Erwinia herbicola*", Journal of Bacteriology, 153: pp. 222-231.

Ng et al. (1962) "Damage and Depression in *Escherichia coli* Resulting from Growth at Low Temperatures", J. Bacteriol, 84: pp. 331-339.

Nowotny (1983) "Shredding Bacteria," Pathological Membranes, Biomembranes, 2: pp. 1-20.

Obata et al. (1989) "Identification of an Ice-nucleating (List continued on next page.)

Primary Examiner—Herbert J. Lilling
Attorney, Agent, or Firm—Burns, Doane, Swecker & Mathis

[57] ABSTRACT

Microbially produced ice nucleator mixtures which include either cell-free ice nucleator particle mixtures and/or whole cell ice nucleator mixtures. These mixtures are produced in methods which comprises culturing a selected microorganism in a two step process at a first temperature in a first step and at a lower temperature in a second step. The mciroorganisms include Erwinia, Pseudomonas and *Escherichia coil.* These methods produce ice nucleator mixtures having increased concentrations of ice nucleating sites per given weight or volume of ice nucleator material.

26 Claims, No Drawings

OTHER PUBLICATIONS

Bacterium and its Ice-nucleating Properties," J. Fermentation and Bioengineering, 67: pp. 143-147.

Parente et al. (1984) "Ultrastructure Aspects of Autolysis of *Pseudomonas fluorescens* Induced by Osmotic Shock" Journal of General Microbiology, 130: pp. 1459-1470.

Phelps et al. (1986) "Release of Cell-free Ice Nuclei by *Erwinia herbiocola*," Journal of Bacteriology, 167: pp. 496-502.

Rosenthal et al. (1976) "Disruption of *Escherichia coli* Outer Membranes by EM 49. A New Membrane Active Peptide Antibiotic," Biochemistry, 26: pp. 5783-5792.

Shaw et al. (1967) "Synthesis of Macromolecules by *Escherichia coli* near the Minimal Temperature for Growth," Journal of Bacteriology, 94: pp. 157-164.

Ward et al., (1989) "Preliminary Experimental Evaluation of Sonomax TM Snow Inducer, *Pseudomonas syringae*, as an Artificial Ice Nucleus for Weather Modification", J. Weather Mod., 21: pp. 9-13.

Watanabe et al. (1987) "Freezing of Water in the Presence of the Ice Nucleation Active Bacterium, *Erwinia ananas*, and its Applicataion for Efficient Free-drying of Foods," Agric. Biol. Chem., 51: pp. 557-563.

The Weather Modification Association (1984) "Weather Modification Some Facts about Seeding Clouds", pp. 1-17.

Wensink et al. (1981) "Outer-Membrane Vesicles Released by Normally Growing *Escherichia coli* Contain Very Little Lipoprotein," Eur. J. Biochem., 116: pp. 331-335.

Woodley et al. (1990) "Atmospheric Tests of an Organic Nucleant in a Supercooled Fog", J. Weather Mod., 22: pp. 127-132.

Yankofsky et al. (1981) "Association with Citrus of Ice-Nucleating Bacteria and Their Possible Role as Causative Agents of Frost Damage" Current Microbiology, 5: pp. 213-217.

Yankofsky et al. (1983) "Induction of Latent Freezing Nucleus Capability in an Ice-nucleation Bacterium," Current Microbiology, 9: pp. 263-267.

Ruggles (1991) "Probing the Cell Surface Exposure of Bacterial Ice Nuclei"-Ph.D. Thesis, University of Colorado; pp. 1-36.

Watanabe et al. (1989) "Freeze Concentration of Some Foodstuffs Using Ice Nucleation-active Bacterial Cells Entrapped in Calcium Alginate Gel", Japan Soc. Biosci., 113: pp. 2731-2735.

Krieg et al. (1989) Bergey's Manual of Systematic Bacteriology, Williams & Wilkins, Baltimore, Md., vol. 1: pp. 141-148.

Difco Manual of Dehydrated Culture Media and Reagents for Microbiological and Clinical Laboratory Procedures, (1977) Difco Laboratories, Detroit, Mich., Ninth Ed: p. 127.

Maki et al. (1978) "Bacteria a Biogenic Source of Freezing Nuclei" Journal of Applied Meteorology, 17: pp. 1049-1053.

Lindow et al. (1978) "*Erwinia herbicola:* A Bacterial Ice Nucleus Active in Increasing Frost Inquiry to Corn", Phytopathology, 68: pp. 523-528.

Vining, (1983) Biochemistry and Genetic Regulation of Commercially Imported Antibiotics, Addison-Wesley Publishing Co., Reading, Mass.; pp. 196-197 127.

Stanbury et al., (1984) Principles of Fermentation Technology, Pergamon Press, Oxford, pp. 22-24.

Goldstein et al. "Biochem" vol. 87 pp. 283-287 Jan. 1990.

Jones et al. "Jour. Bacteriology" May 1987 pp. 2092-2095.

CELL-FREE AND WHOLE CELL ICE NUCLEATORS AND PROCESS FOR THEIR PRODUCTION

BACKGROUND OF THE INVENTION

The present invention relates to ice-nucleators and, more particularly, to microbially produced ice-nucleators which are either whole cell or cell-free.

It has been known for years that certain microorganisms are capable of acting as nucleating agents for the formation of ice. A number of practical applications exist for exploiting such ice nucleating ability including inducing precipitation (e.g., cloud seeding) and snowmaking. Furthermore, the role of ice nucleating microorganisms in inducing frost injury to plants has been investigated. To date, the art has employed both the microorganisms themselves (whole cell products) and products derived from such microorganisms (cell free products).

When the microorganisms themselves are employed to form a whole cell product, it has been found desirable in cloud seeding to provide such microorganisms in a dried form because dried microorganisms can act as very efficient condensation nuclei which adsorb water very readily at low levels of water vapor supersaturation. Thus, U.S. Pat. No. 4,706,463 relates to the recovery of microorganisms having ice nucleating activity, in dried form. Prior methods of culturing microorganisms having ice nucleating activity were discussed. Such methods, while acknowledged to enable production of large volumes of microorganisms, were said to be inadequate in producing a dried product because much of the activity is lost during the drying of large volumes of the material. A process was therefore proposed for preserving the ice nucleating activity after drying of any suspension containing the microorganisms. Such method involves the steps of (a) bringing the temperature of said medium to a temperature of about 15° C. or less, (b) forming a concentrate of the microorganism preferably having a water content of about 15-27%, while maintaining the temperature of about 15° C. or less, (c) running the concentrate into a cryogenic liquid in the form of a fine stream so as to form frozen pellets of the concentrate preferably having a diameter of about 2-10 mm, and (d) freeze drying the pellets at a temperature below 25° C.

Another whole cell product including ice nucleating activity is produced by fermenting a microorganism having ice nucleating activity. The microorganism is grown at a temperature of at least about 29° C. in a medium until the stationary phase. Fermentation is continued during the stationary phase at a temperature below about 24° C. The amount of nitrogen source in the growth medium should be low enough so that, at the conclusion of the growth phase, there is insufficient nitrogen source remaining to inhibit the formation of ice nucleating activity during the subsequent phase. It was found that INA is produced predominantly during the stationary phase of the fermentation if the temperature during such phase is maintained below 24° C. Suitable microorganisms that have ice nucleation activity include Pseudomonas such as *P. syringae* and *P. fluorescens, P. coronafaciens* and *P. pisi*. Other microorganisms that are useful include *Erwinia herbicola*.

As previously indicated, methods have also been proposed for preparing cell free ice nucleating agents. For example, a cell-free method has been developed that helps to increase the ice nucleation active particle number per gram of a dried bacterial culture. The method entails the fluid energy mill grinding of a dry bacterial culture in order to produce a dry talcum like powder that approaches near single cell size distribution upon aerosolization. This is advantageous to the cloud seeding industry since it increases the number of active ice nuclei per particle of seeding material.

U.S. Pat. No. 4,464,473 describes isolation of DNA segments encoding for substances having ice nucleation activity (INA). The DNA is isolated from organisms known to provide for ice nucleation such as various species of Pseudomonas including syringe, coronafaciens, pisi, tabaci or fluorescens. Xanthomonas, such as translucens or Erwinia, such as herbicola can also be employed. The host is then transformed with the DNA and the substances having ice nucleation activity expressed by the host microorganism. According to the disclosure, organisms which have a wide variety of ecological niches can be modified so as to provide for ice nucleation activity in new environments and/or with higher efficiency.

Phelps, et al., in "Release of Cell-Free Ice Nuclei by *Erwinia herbicola*", J. Bact. 167(2): 496–502 (1986), employs *Erwinia herbicola* or *Pseudomonas syringae* for probing cell surfaces for ice nuclei. Cell free ice nuclei were isolated by growing the bacteria in DM glucose medium at 15° C. to stationary phase and by collecting supernatant by centrifugation and filtration through a 0.22 mμ filter.

The advances in various whole cell and cell-free products notwithstanding, the art continues to seek out ice nucleators which exhibit a number of desirable properties. Included among such properties are (1) a high number of ice nucleating sites per gram of material; (2) a high number of ice nucleating sites per milliliter of material; (3) a high amount of ice nucleating activity per gram of protein; and (4) a high degree of stability at 37° C.

SUMMARY AND OBJECTS OF THE INVENTION

In view of the continuing need in the art for ice nucleating agents meeting the criteria set forth above, it is a primary objective of the present invention to fulfill such need by providing novel methods for producing whole cell and cell free ice nucleators, novel whole cell and cell free nucleators produced by such methods, and methods for making snow or seeding clouds using such nucleators.

More particularly, it is an object of the present invention to provide ice nucleators, both whole and cell free, which are highly concentrated (in terms of the number of ice nucleating sites per a given weight or volume of material).

It is a further object of the present invention to provide ice nucleators, both whole and cell free, which are highly stable at a temperature of 37° C.

In a first aspect, the present invention relates to a process for producing a cell-free ice nucleator comprising the steps of:

(i) culturing a blebing microorganism capable of producing an ice-nucleator protein, said culturing being carried out at a first temperature promoting growth phase of said microorganism and being continued until stationary phase:

(ii) culturing said blebing microorganism, during stationary phase, at a second temperature below said first temperature effective to promote production of active cell-free ice nucleator protein;

(iii) separating active cell-free ice-nucleator agent from said microorganism.

In another aspect, the present invention relates to a process for producing a whole cell/cell free ice nucleator protein mixture comprising the steps of:

(i) culturing a blebing microorganism capable of producing an ice-nucleator protein, said culturing being carried out at a first temperature promoting growth phase of said microorganism and being continued until stationary phase:

(ii) culturing said blebing microorganism, during stationary phase, at a second temperature below said first temperature effective to promote production of active cell-free ice nucleator protein.

In a first product aspect, the present invention relates to a cell-free ice nucleator agent produced by the process described above.

In a second product aspect, the invention relates to a whole cell/cell free ice nucleator protein mixture produced by the process described above.

In a first method of use aspect, the present invention relates to a method for making snow comprising adding an effective amount of the ice nucleator protein as described above to water.

In a second method of use aspect, the present invention relates to a method for seeding a cloud comprising adding the ice nucleator protein as described above to a cloud.

With the foregoing and other objects, advantages, and features of the invention that will become hereinafter apparent, the nature of the invention may be more clearly understood by reference to the following detailed description of the invention, and to the appended claims.

DETAILED DESCRIPTION OF PREFERRED EMBODIMENTS

The process for producing cell free ice-nucleators or mixtures of cell free and whole cell ice nucleators is discussed first.

First, a microorganism capable of producing a cell free ice nucleating agent is cultured. The present inventors have found that (1) certain microorganisms which produce ice nucleator protein also form "blebs" which are little bud like protrusions formed in the cell wall of a microorganism and (2) when cultured under the right conditions, such "blebs" not only break away from the whole cell but, in addition, such blebs contain a significant amount of the ice nucleator protein produced by the cell. Thus, a subsequent separation of the whole cells from the medium will yield a large quantity of cell free ice nucleator protein in the form of these blebs. Of course, it is also possible to employ the whole cells in combination with the blebs which have formed.

Included among microorganisms known in the art to both form ice nucleator protein and blebing are those of the species Erwinia. E. Coli, and Pseudomonas. Preferred is Erwinia ananas.

Growth mediums which are suitable for culturing the microorganism capable of producing an ice nucleating agent generally include the following components:

| | |
|---|---|
| Carbon source | 15–50 g/l |
| Nitrogen source | 20–60 g/l |
| Magnesium salt | 0.4–8 g/l |
| Zinc salt | 0.2–4 g/l |
| Phosphate salt | 0.02–6 g/l |
| Antifoam agent | 0.1–2 g/l |

The preferred nitrogen source is MSG. The initial concentration of the nitrogen source is related to the temperature of the fermentation during the growth phase. There should be enough nitrogen source present to provide a final cell mass of at least about 20 g/l. However, there should not be so much that there is inhibitory amounts of nitrogen source left over after the growth phase is completed. The amount is related to the temperature since as the temperature is increased, the potential for cell mass is also increased up to a point and the nitrogen source must be increased correspondingly. As the optimum growth temperature for the microorganism is exceeded, the potential for growth decreases and the nitrogen source must be decreased accordingly.

The amount of nitrogen source remaining at the conclusion of the growth phase can be measured using conventional methods. The exact method used will depend on the nature of the nitrogen source. Where MSG is the source, it can be measured in the medium by an HPLC method using an OPA-mercaptoethanol fluorescent derivative as is known in the art.

The nitrogen source should be low enough so that, at the conclusion of the growth phase, there is insufficient nitrogen source remaining to inhibit the formation of ice nucleating activity during the subsequent stationary phase.

It is also necessary to limit the amount to phosphate in the growth medium. More specifically, there should be just enough phosphate present in the initial medium to go to the stationary phase of growth. Amounts of phosphate in excess of this minimal amount have been observed to inhibit INA formation. A useful range of initial phosphate concentration is between about 0.2 to 6 g/l, preferably 0.6 to 3 g/l. In a preferred embodiment, the initial phosphate concentration is selected so that little, e.g., less than 1 g/l remains at the conclusion of the growth phase. Potassium phosphate is preferred.

As carbon source, there may be employed sugars such as glucose (or crude glucose such as dextrose), sucrose, fructose, erythrose, mannose, xylose, and ribose. Commercial sources of these sugars can conveniently be used. Such sources include liquid sucrose, high fructose corn syrup and dextrose corn syrup. Mixtures of these sugars can also be used. Other carbon sources can be used in combination with these sugars such as mannitol and other sugar derivatives.

The medium preferably further includes other components useful in fermentation processes including a source of magnesium such as magnesium sulfate, a source of iron such as iron sulfate, and a source of zinc such as zinc sulfate.

In the fermentation of the present microorganisms as well as other microorganisms, there occurs what is called the growth phase where the microorganism is multiplying rapidly. This phase is also known in the art as the "log phase" or logarithmic growth phase. During this period, if the logarithm of the optical density of the growth medium is plotted versus time, a straight line will result. At the end of this period, the slope of this line will decrease dramatically indicating that the microorganism is no longer proliferating, i.e., the stationary phase is reached. There is a brief transition between these two phases. In a typical fermentation lasting for 22 hours, for example, the transition may last only one hour. Thus, the end of growth phase as understood in the context of the present application corresponds to the time spanning from about the end of the straight line portion through the brief transition period.

The microorganism is cultured in two stages. The first stage is carried out at a temperature sufficient to promote growth phase of the microorganism. Such temperature range is readily determined for any species of microorganism which produces INA and forms blebs. Generally, for a species such as *E. ananas*, the temperature should range between about 25° and 42° C. and preferably should be about 35° C. At such temperature, growth will proceed rapidly. Above 42° C., the desired final INA protein product is not obtained. Below about 25° C., good growth is not observed. During the rapid growth phase, the pH of the medium typically ranges between about 5 and 7. Additionally, the dissolved oxygen level typically ranges between 0 and 100. After a certain period of time, however, the level of growth will taper off. Such tapering off is accompanied by a drop in the pH as well as by a rise in the dissolved oxygen level. Such condition corresponds to "rollover", i.e, entry into the stationary phase.

After rollover, the temperature of the growth medium is reduced to a temperature effective to promote production of active cell-free ice nucleator protein. This corresponds to a temperature of between about 0° and 20° C. In the case of the preferred embodiment wherein *E. ananas* is employed as the microorganism, the temperature is lowered from about 35° C. to about 15° C. at rollover. The medium is maintained at the reduced temperature for a period of time sufficient to maximize production of the cell free ice nucleator. Typically, such period of time will be between 24 and 72 hours. Culturing is stopped once protein production is observed to stop.

Depending on whether the cell free or the whole cell products are desired, the final medium is then subjected to a variety of steps to recover the desired ice nucleating agent.

Where the cell free product is desired, the broth may be centrifuged and the resulting liquid passed through a filter capable of removing the cells, e.g., a 0.22 μm filter. The whole cell product, of course, can be obtained directly from the broth.

The final products, whether cell free or the whole cell, can be employed in methods for making snow or in methods for seeding clouds in accordance with techniques well known to persons skilled in the art.

The following examples are given in order to illustrate preferred embodiments of the invention and in no way should be construed as limiting the subject matter disclosed and claimed.

EXAMPLE 1

Preparation of a cell free ice nucleator derived from *E. sps*

A 1.5 ml frozen sample of Erwinia ananas was used to inoculate a fernbach which in turn was used to inoculate a small fermenter. The same medium was used for both namely:

| Sucrose | 25.5 g/l |
|---|---|
| MSG | 33 g/l |
| MgSO$_4$.7H$_2$O | 4 g/l |
| ZnSO$_4$.7H$_2$O | 2 ml/l |
| KH$_2$PO$_4$$^-$ | 0.49 g/l |
| FeSO$_4$.7H$_2$O$^-$ | 0.112 g/l |
| antifoam | 1 ml/l |

The medium was mixed together in the order listed, with 200 ml going to the Fernbach and 800 ml going to the fermenter. The Fernbach was autoclaved for 20 minutes and the tank autoclaved for 40 minutes. After allowing the Fernbach to cool, one frozen vial of the *Erwinia ananas* was added, and incubated at 35° C. with agitation at 150 rpm for 12 hours. The initial optical density (OD) at 600 nm of the Fernbach was taken after 12 hours and should be between 10 and 20 OD. The zero hour OD in the tank should be about 2 after inoculation using the correct amount from the Fernbach. The formula for this is: OD(Fernbach) * x ml/800 ml (Tank Volume)=initial OD of 2.

The conditions in the tank were: Temperature=35° C.; Agitation=500 rpm (as cells grow, the rpm went up), air flow=1 l pm, pH=5.5-6.6 (controlled with 4N H$_2$SO$_4$ and 2N NaOH). At about an elapsed fermentation time (EFT)=8-10 hours, cell growth leveled off, pH dropped about 1 pH unit, and the dissolved oxygen (DO) level rose. These conditions comprised rollover. The temperature was then switched to 15° C. for 16 hours, the other conditions remaining the same. At EFT=24 hours, a sample of the broth was removed and stored at 4° C. for Ice Nucleator Activity (INA) testing. The tank ran until EFT=72 hours.

To recover INA product, the sample broth was centrifuged in microcentrifuge tubes at the highest speed setting for 5 minutes. Some of the sample was then filtered through a 0.22 μm filter to remove the cells. Both the filtered and unfiltered samples, and the whole cell broth (WCB) were tested for their INA activity. All samples were plated for contamination on tryptic soy agar (TSA) plates. Samples were also run on an electrophoresis gel, sent out for carbon, nitrogen, and salts composition, stability at 37° C., and ice nucleating activity per gram of material.

The results, which are presented in Table 1 below, clearly demonstrate the improvements obtained in terms of several important criteria including ice nucleating sites per both weight and volume of material and stability at 37° C.

COMPARATIVE EXAMPLE 1

Preparation of a cell free ice nucleator derived from *E. herbicola* according to the method of Fall et al.

Six 125 ml baffled shake flasks were inoculated with 1.5 ml frozen *Erwinia herbicola*. Twenty five ml of minimal media was used including:

| K$_2$HPO$_4$ | 7 g/l |
|---|---|
| KH$_2$PO$_4$ | 3 g/l |
| (NH)$_2$SO$_4$ | 1 g/l |
| Sodium Citrate | 0.5 g/l |

These components were mixed together, the pH adjusted to 7.4 with 2N NaOH, and autoclaved for 20 minutes. MgSO$_4$·7H$_2$O (0.1 g/l), glycerol (9.2 g/l) were mixed together and filter sterilized through a 0.22 μm filter. These two components were added to the cool autoclaved portion.

The flasks were incubated at 22° C. for about 12 hours. The OD after 12 hours was about 4-5. The six flasks were combined together and this pooled broth used to inoculate ten 500 ml shake flasks with 50 ml of the same minimal medium as in step one. The inoculation amount is calculated in the same way that the inoculum was calculated above for the product of the invention.

The ten flasks were incubated at 22° C. and agitated at 150 rpm for 4 hours. To five of the flasks, mitomycin C was added. The other five flasks were used as controls. After the addition of mitomycin C, the flasks must be kept in the dark. After 4 hours in the dark the temperature was dropped to 4° C. with no agitation overnight. The next day, a sample was tested in the same way that the samples of the invention were tested.

A comparison of the results between the cell free ice nucleators of the invention and those of Fall et al is presented below:

RESULTS:
EXAMPLE 1 AND COMPARATIVE EXAMPLE 1

|  | EX 1 | COMP. EX 1 |
|---|---|---|
| Ice-Nucleating Sites Per Gram | $6.9 \times 10^{8}$ | $9.9 \times 10^{5}$ |
| Ice-Nucleating Sites Per ml | $2 \times 10^{6}$ | $5.6 \times 10^{2}$ |
| G Protein/G Material | $6.9 \times 10^{-4}$ | $1.6 \times 10^{-5}$ |
| G Carbon/G Material | $3.6 \times 10^{-4}$ | $1.5 \times 10^{-4}$ |
| G Nitrogen/G Material | $3.1 \times 10^{-6}$ | $1.8 \times 10^{-5}$ |
| % Salts (Cations) | 4.1% | 25.2% |
| % Proteins | 6.8% | 1.6% |
| Stability After 37 Deg. Temperature Change (0-37 Deg. C.) Measured As INA/ml | | |
| Before Change | 5.42 | 2.75 |
| After Change | 5.35 | 0 |

EXAMPLE 2

Growth of *E. herbicola* strain GR-B in Bleb Optimum Media

The effect of variations in the growth medium was examined.

Materials 1. 1-2.0 L New Brunswick fermentor.
2. Bleb Optimum media materials.
3. INA assay materials.
4. 1 baffled fernbach.
5. 1 ml frozen vial of strain GR-B.
6. Air hookup for fermentor.
7. Cooling water for fermentor.
8. 1.0 L each of 2N NaOH and 2 $H_2SO_4$ in separate containers, also sterile.
9. Incubator set at 35° C. for seed fernbach.
10. 1.0 L of 0.9% sterile saline solution.
11. Tryptic soy agar plates (TSA).
12. pH meter and probe.
13. DO (dissolved oxygen) meter and probe.
14. 0.22 μm (low affinity binding) filters.
15. Syringes—10 ml.
16. Microcentrifuge tubes—sterile.

Procedure:
Make up media:

| Formula | Sucrose - 25 g/l |
|---|---|
| add components in this order bringing total volume to 1.0 l with milli-q water 800 ml are added to the tank and 200 ml are added to fernbach | MSG - 36 g/l<br>$MgSO_4$—$7H_2O$ - 4 /gl<br>$ZnSO_4$—$7H_2O$ - 0.0024 g/l<br>$KH_2PO_4$ - 0.58 g/l<br>$FeSO_4$—$7H_2O$ - 0.112 g/l<br>Mazu - 0.1 ml/l |

Autoclave the 200 ml in the fernbach for 20 minutes (cover fernbach with 2 layers of gauze) and the tank for minutes (make sure all the open ports of the fermentor are clamped off except for the outlet air).

After the fernbach has cooled add 1.0 ml of frozen GR-B stock to it. Incubate it at 35° C., rpm-150 overnight, 13 hours.

Let the tank cook, then hook it up to the inlet and outlet water supply and the inlet and outlet air hoses.

13 hours later, remove the fernbach and take a OD reading and plate some of the broth on TSA plate.

From the OD reading calculate what amount of the fernbach broth will be needed to add to the tank to give a starting OD=2.

$$\frac{(OD \text{ of fernbach}) \times (X \text{ ml})}{(\text{volume of fermentor})} = 2(\text{desired starting } OD)$$

Aseptically add the calculated amount to the tank setting the temperature at 35° C., air flow=ILPM, pH control at 5.5-6.6 (that is what the acid and base are for), agitation at 500 rpm, this will go up as the bacteria starts to grow.

Take a 0+ sample, then a sample every 2 hours until rollover occurs, usually at 8 hours, which is a condition consisting of a drop in dissolved oxygen, then a 1 unit drop in pH.

When rollover occurs drop the tank temperature to 15° C. and leave until 24 hours (EFT).

At 24, 48, and 72 hours remove 5-10 ml of sample and do INA assay on the whole cell broth and cell-free filtrate. A cell-free filtrate is obtained by first putting 1.7 ml of broth into a microcentrifuge tube, centrifuging for 5 minutes, then aseptically pushing the sample through a 0.22 μm filter. A supernatant sample was also tested. It too was spun down but for 10 minutes and was not filtered.

Plate at 24, 48, and 72 hours on TSA plates for contamination. Plate whole cell broth, filtrates, and supernatant. Incubate at 30° C. for 24 hours.

Whole cell broth and filtrate samples were saved for stability testing. Results: The cells reached a maximum OD of about 26 at EFT=30 hours, at rollover the OD was 23. There was no growth on the filtrate plates, no contaminating growth on the whole cell broth plates, just *E. herbicola* growth, the average cell growth on the supernatant plates was about 350 colonies—this means that centrifuging not remove all the cells but filtering did.

| Time (EFT) | INA Results: | | |
|---|---|---|---|
|  | WCB | Filtrate | Supernatant |
| 12 | 10.12 | 4.84 | — |
| 24 | 10.43 | 5.30 | — |
| 30.5 | 10.79 | 6.20 | — |
| 36 | 10.71 | 6.80 | — |
| 48 | 10.80 | 6.96 | — |
| 56 | 11.02 | 6.90 | 7.71 |

-continued

| | INA Results: | | |
|---|---|---|---|
| Time (EFT) | WCB | Filtrate | Supernatant |
| 72.5 | 10.55 | 7.16 | 8.80 |
| 120 | 10.36 | 7.25 | 7.25 |

Stability Results

INA from 72.5 hour sample was left at room temperature for 48 hours.—WCB—8.55 Supernatant—7.10

Loss of WCB activity—10.55 to 8.55—2 log unit loss. filtrate=7.16-7.10—no activity loss. supernatant=8.80-7.10—about 1.5 log unit loss.

Stability of filtrate after 5 minutes at 37° C.

Time 0=INA=5.42—after 5 minutes at 37° C.=5.35

This is equal to 15% loss in activity. Such reduction in activity is far lower than that achieved by Ruggles et al.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. A process for producing a cell-free ice nucleator particle mixture comprising the steps of:
   i) selecting a microorganism from the group consisting of Erwinia, Pseudomonas and Escherichia coli, wherein the microorganism produces blebs and ice nucleating protein;
   ii) culturing said microorganism from step (i) in defined medium comprising the following components:

| | |
|---|---|
| carbon source | 15-50 g/l |
| nitrogen source | 20-60 g/l |
| magnesium salt | 0.4-8 g/l |
| zinc salt | 0.4-4 g/l |
| phosphate salt | 0.02-6 g/l | at a first temperature sufficient to promote growth of said microorganism and for a period of time sufficient to achieve stationary phase;
   iii) culturing said microorganism from step (ii), at a second temperature below said first temperature effective to promote production of active cell-free ice nucleator protein; and
   iv) separating cell-free ice nucleator particles from said microorganisms.

2. The process according to claim 1 wherein said microorganism is *Erwinia ananas* or *Erwinia herbicola*.

3. The process according to claim 1 wherein said nitrogen source is present in an amount low enough such that, at the conclusion of said step (ii), there is insufficient nitrogen source remaining to inhibit production of ice nucleator protein during said stationary phase.

4. The process according to claim 1 wherein said phosphate salt is present in an amount low enough such that, at the conclusion of said step (ii), there is insufficient phosphate salt remaining to inhibit production of ice nucleator protein during said stationary phase.

5. The process according to claim 1 wherein said step (ii) is carried out at a temperature between about 25° and 42° C.

6. The process according to claim 2 wherein the temperature in said step (iii) is reduced to between about 0° and 22° C.

7. The process according to claim 1 wherein said ice-nucleator particles are removed from said microorganisms in step (iv) by filtration.

8. A process for producing a whole cell ice nucleator particle mixture comprising the steps of:
   i) selecting a microorganism from the group consisting of Erwinia, Pseudomonas and *Escherichia coli* wherein the microorganism produces blebs and ice nucleating protein;
   ii) culturing said microorganism from step (i) in defined medium comprising the following components:

| | |
|---|---|
| carbon source | 15-50 g/l |
| nitrogen source | 20-60 g/l |
| magnesium salt | 0.4-8 g/l |
| zinc salt | 0.4-4 g/l |
| phosphate salt | 0.02-6 g/l | at a first temperature sufficient to promote growth of said microorganism and for a period of time sufficient to achieve stationary phase;
   iii) culturing said microorganism from step (ii), at a second temperature below said first temperature effective promote production of active cell-free ice nucleator protein.

9. The process according to claim 8 wherein said microorganism is *Erwinia ananas* or *Erwinia herbicola*.

10. The process according to claim 8 wherein said nitrogen source is present in an amount low enough such that, at the conclusion of said step (ii), there is insufficient nitrogen source remaining to inhibit production of ice nucleator protein during said stationary phase.

11. The process according to claim 8 wherein said nitrogen source is monosodium glutamate.

12. The process according to claim 8 wherein said phosphate salt is present in an amount low enough such that, at the conclusion of said step (ii), there is insufficient phosphate salt remaining to inhibit production of ice nucleator protein during said stationary phase.

13. The process according to claim 8 wherein said step (ii) is carried out at a temperature between about 25° and 42° C.

14. The process according to claim 8 wherein said step (iii) is carried out at a temperature between about 0° and 22° C. for about 24 to 72 hours.

15. The process according to claim 1 wherein said ice nucleator particles are removed from said microorganisms in step (iv) by centrifugation.

16. The process according to claim 1 wherein said nitrogen source is monosodium glutamate.

17. A process for producing a whole cell ice nucleator particle mixture comprising the steps of:
   i) selecting a microorganism from the group consisting of Erwinia, Pseudomonas and *Escherichia coli* where the microorganism produces blebs and ice nucleating protein;
   ii) culturing said microorganism from step (i) in medium at a temperature of between about 25°-42° C. for a period of time sufficient to achieve stationary phase;

iii) culturing said microorganism from step (ii), at a temperature of about 0°-22° C. for about 24 to 72 hours;

wherein said medium comprises a nitrogen source present in an amount low enough such that, at the conclusion of step ii), there is insufficient nitrogen source remaining to inhibit production of ice nucleator protein during step iii).

18. The process of claim 17 wherein the medium comprises the following composition:

| | |
|---|---|
| carbon source | 15-50 g/l |
| nitrogen source | 20-60 g/l |
| magnesium salt | 0.4-8 g/l |
| zinc salt | 0.4-4 g/l |
| phosphate salt | 0.02-6 g/l |

19. The process according to claim 18 wherein said nitrogen source is monosodium glutamate.

20. The process according to claim 18 wherein said phosphate salt is present in an amount low enough such that, at the conclusion of said step (ii), there is insufficient phosphate salt remaining to inhibit production of ice nucleator protein during said stationary phase.

21. A process for producing a cell free ice nucleator particle mixture comprising the steps of:
i) selecting a microorganism from the group consisting of Erwinia, Pseudomonas and *Escherichia coli* wherein the microorganism produces blebs and ice nucleating protein;
ii) culturing said microorganism from step (i) in medium at a temperature of between about 25°-42° C. for a period of time sufficient to achieve stationary phase;
iii) culturing said microorganism from step (ii), at a temperature of about 0°-22° C. for about 24 to 72 hours;
iv) separating active cell-free ice-nucleator particles from said microorganisms;

wherein said medium comprises a nitrogen source present in an amount low enough such that, at the conclusion of step ii), there is insufficient nitrogen source remaining to inhibit production of ice nucleator protein during step iii).

22. The process of claim 21 wherein the medium comprises the following composition:

| | |
|---|---|
| carbon source | 15-50 g/l |
| nitrogen source | 20-60 g/l |
| magnesium salt | 0.4-8 g/l |
| zinc salt | 0.4-4 g/l |
| phosphate salt | 0.02-6 g/l |

23. The process according to claim 21 wherein said nitrogen source is monosodium glutamate.

24. The process according to claim 22 wherein said phosphate salt is present in an amount low enough such that, at the conclusion of said step (ii), there is insufficient phosphate salt remaining to inhibit production f ice nucleator protein during said stationary phase.

25. The process according to claim 21 wherein said active ice nucleator particles are removed from said microorganisms in step (iv) by centrifugation.

26. The process according to claim 21 wherein said active ice nucleator particles are removed from said microorganisms in step (iv) by filtration.

* * * * *

UNITED STATES PATENT AND TRADEMARK OFFICE
CERTIFICATE OF CORRECTION

PATENT NO. : 5,223,412
DATED : June 29, 1993
INVENTOR(S) : Wight et al.

It is certified that error appears in the above-indentified patent and that said Letters Patent is hereby corrected as shown below:

Abstract, line 4, where "comprises" should read --comprise--;
    lines 7 and 8, where "Erwinia, Pseudomonas" should read
    --Erwinia, Pseudomonas--.

Column 1, line 63, where "Pseudomonas" should read --Pseudomonas--.

Column 2, lines 13-15, where "Pseudomonas including syringe,
    coronafaciens, pisi, tabaci or fluorescens. Xanthomonas, such
    as translucens or Erwinia, such as herbicola" should read
    --Pseudomonas including syringe, coronafaciens, pisi, tabaci or
    fluorescens. Xanthomonas, such as translucens or Erwinia, such
    as herbicola--.

Column 3, line 43, where "ice-nucleators" should read --ice nucleators--;
    line 61, where "Erwinia" should read --Erwinia-- and "Psuedomonas"
    should read --Pseudomonas--; line 62, where "Erwinia ananas" should
    read --Erwinia ananas--.

Column 4, line 35, where the second occurrence of "to" should read
    --of--.

Column 5, line 65, where "Erwinia ananas" should read --Erwinia ananas--.

Column 6, line 25, where "1 1 pm" should read --1 lpm--; line 63,
    where "(NH)$_2$SO$_4$" should read --(NH$_4$)$_2$SO$_4$--.

Column 7, line 20, where "al" should --al.--.

UNITED STATES PATENT AND TRADEMARK OFFICE
CERTIFICATE OF CORRECTION

PATENT NO. : 5,223,412
DATED : June 29, 1993
INVENTOR(S) : Wight et al.

It is certified that error appears in the above-indentified patent and that said Letters Patent is hereby corrected as shown below:

Column 8, line 12, where --45-- should be inserted after "for"; line 30, where "ILPM" should read --1 LPM--; line 58, where --did-- should be inserted before "not".

Column 9, line 31, where "Erwinia, Pseudomonas and Escherichia coli" should read --Erwinia, Pseudomonas and Escherichia coli--; line 41, where "0.4-4 g/l" should read --0.2-4 g/l--; line 44, where "and" should be deleted; line 48, where "active" should be deleted.

Column 10, line 10, where "Erwinia, Pseudomonas" should read --Erwinia, Pseudomonas-- line 21, where "0.4-4 g/l" should read --0.2-4 g/l--; line 29, where --to-- should be inserted after "effective"; line 47, where "according to" should read --of--; line 62, where "Erwinia, Pseudomonas" should read --Erwinia, Pseudomonas--; line 63, where "where" should read --wherein--.

Column 11, line 17, where "0.4-4 g/l" should read --0.2-4 g/l--; line 31, where "Erwinia, Pseudomonas" should read --Erwinia, Pseudomonas--.

Column 12, line 19, where "0.4-4 g/l" should read --0.2-4 g/l--; line 22, where "21" should read --22--; line 27, where "f" should read --of--.

Signed and Sealed this

Twenty-second Day of November, 1994

Attest:

BRUCE LEHMAN

*Attesting Officer*    *Commissioner of Patents and Trademarks*